United States Patent [19]

Davies

[11] Patent Number: 4,905,708

[45] Date of Patent: Mar. 6, 1990

[54] APPARATUS FOR RECOGNIZING CARDIAC RHYTHMS

[76] Inventor: David W. Davies, St. Bartholomews Hospital, West Smithfield, London, E.C.1., England

[21] Appl. No.: 100,722

[22] Filed: Sep. 24, 1987

Related U.S. Application Data

[63] Continuation-in-part of Ser. No. 793,538, Oct. 31, 1985, abandoned.

[51] Int. Cl.$^4$ ................................................ A61B 5/04
[52] U.S. Cl. .............................. 128/705; 128/419 PG
[58] Field of Search .................................. 128/702–703

[56] References Cited

U.S. PATENT DOCUMENTS

| 3,524,442 | 8/1970 | Horth | 128/2.06 |
|---|---|---|---|
| 3,606,882 | 9/1971 | Abe et al. | 128/2.06 A |
| 3,616,791 | 11/1971 | Harris | 128/2.06 A |
| 3,618,593 | 11/1971 | Nachev et al. | 128/2.06 A |
| 3,699,946 | 10/1972 | Michel | 128/2.06 A |
| 3,858,034 | 12/1974 | Anderson | 235/151.3 |
| 3,978,856 | 9/1976 | Michel | 128/2.06 A |
| 4,458,692 | 7/1984 | Simson | 128/705 |
| 4,546,776 | 10/1985 | Bellin et al. | 128/704 |
| 4,589,420 | 5/1986 | Adams et al. | 128/702 |
| 4,704,681 | 11/1987 | Shimizu et al. | 128/704 |
| 4,742,458 | 5/1988 | Nathans et al. | 128/703 |

FOREIGN PATENT DOCUMENTS 204330 11/1983 Fed. Rep. of Germany .

OTHER PUBLICATIONS

Conference Proceedings of the Conference on the Application of Electronics in Medicine, Southampton Hants, England–"A Recognition System for the Detection of Cardiac Arrhythmias", D. G. Kyle et al., pp. 223–228.

Primary Examiner—William E. Kamm
Attorney, Agent, or Firm—Hill, Van Santen, Steadman & Simpson

[57] ABSTRACT

Apparatus for recognizing cardiac arrhythmias digitalises analog signals which are obtained when carrying out sensing at the heart or on the body and carries out a first differentiation of the digitalised signals. A gradient pattern detector compares the differentiated signals thereby produced with normal differentiated signals detected during sinus rhythm as to amplitude, polarity and sequence. Differences between the differentiated signals will be indicative of pathological tachycardias, the nature of which will be identified by comparison with pre-programmed signals of like type and a response to terminate the arrhythmia can be delivered to the heart.

7 Claims, 4 Drawing Sheets

APPARATUS FOR RECOGNIZING CARDIAC RHYTHMS

BACKGROUND OF THE INVENTION

Cross Reference to Related Applications

The present application is a continuation-in-part of Ser. No.793,538 filed Oct. 31, 1985, and now abandoned.

This invention relates to apparatus for recognizing cardiac rhythms. The invention relates in particular, but not exclusively, to cardiac implants, generally known as pacemakers, for detecting and providing corrective response to cardiac arrhythmias, in particular pathological tachycardia.

Pacemaker recognition of pathological tachycardia generally relies on heart rate analysis. More specifically, current pacemaker sensing amplifiers are relatively unsophisticated in the detection of intracardiac signals, relying entirely upon simple amplitude and frequency bandpass filtration analysis. In the majority of cases, this entails simple detection of a rate which exceeds a preset "trigger" rate. Some devices utilise more refined criteria such as the rate of change of heart rate and sustained high rate which allow more ready distinction between physiological and pathological tachycardia. However, diagnosis is still difficult, particularly when pathological tachycardia emerges from a background of sinus tachycardia and when sinus tachycardia follows successful termination of pathological tachycardia.

The overlap between the heart rates occurring during sinus and pathological tachycardia in some patients has presented a problem in recognition of one from the other by implanted devices because of the reliance placed upon heart rate analysis for making the diagnosis. Despite refinement in the heart rate criteria examined, pathological tachycardia which occurs on exercise and sinus tachycardia following termination of pathological tachycardia poses particular problems. Error in this respect is compounded by devices with an intelligent memory function so that successful extra stimulus timings will not be used readily for subsequent pathological tachycardia because of apparent failure. Also, to make a diagnosis from changes in heart rate requires at least two or more complexes, diagnostic accuracy increasing with the number of complexes counted. These problems would be avoided by a method capable of diagnosing pathological tachycardia independently of changes in the heart rate and from analysis of only one complex.

Frequency analysis of intracardiac electrograms has proved disappointing in this respect, particularly at atrial level and although the results obtained by fast Fourier transformation of the phase spectrum has improved results compared with the use of the more common amplitude spectrum, the computing power required to perform this makes this unattractive as an implantable option because of the increased battery drain that its implementation would involve. Furthermore, this form of recognition is subjective.

SUMMARY OF THE INVENTION

It is an object of this invention to provide apparatus for recognizing pathological tachycardia.

It is another object of the invention to provide apparatus which will enable sinus and pathological tachycardia to be distinguished, which will require only a single complex for diagnosis and which will dictate a response to abnormal rhthyms.

According to the present invention, there is provided an apparatus for recognizing cardiac arrythmias, comprising:

sensing electrode means for attachment to at least one of a heart and a body surface location;

a signal path connecting to the electrode means comprising in series an analog to digital converter means for producing digital signals, means for carrying out a first differentation of the digital signals produced, means for converting the differentiated signals into a readable form and gradient pattern detector means in communication with a memory device means for storing differentiated normal signals detected during sinus rhythm and/or other rhythm; and said gradient pattern detector means comparing deflections of said differentiated signals as to their amplitudes, polarities, durations, separation and sequence with respect to said differentiated normal signals stored in the memory device means.

The present invention encompasses both implants modified to embody this invention and apparatus for use under clinical conditions comprising sensors to be applied internally or externally to the heart or to the body surface for monitoring for cardiac arrhythmias in general. Preferably the apparatus includes a source of cardiac electrical stimuli and is programmed to produce or withhold such stimuli which will terminate or prevent arrhythmia.

The apparatus of this invention is suitable for distinguishing sinus from abnormal cardiac depolarisations at both atrial and ventricular level. Although previously attempts have been made at distinguishing sinus from abnormal cardiac depolarisations at both atrial and ventricular level, significant differences between rate of change, signal polarities and amplitudes of anterograde and retrograde atrial depolarisations have been found to occur within small patient groups. However even within these groups, the behaviour of these parameters was not always predictable for individual patients and therefore does not represent a useful criterion on which to base reliable automatic recognition of abnormal rhythms.

In contrast to frequency analysis of intracardiac electrograms previously carried out, apparatus of the present invention utilises a principle to be referred to herein as gradient pattern detection. This is a simpler algorithm requiring less in the way of computing power and not reducing implant battery life to the same extent as fast Fourier transformations. Although gradient pattern detection (GPD) consumes battery power additional to that consumed when detection of arrhythmias takes place using conventional methods it is not necessary to operate continuously the apparatus embodying this invention. GPD will only need to be operated when trigger heart criteria are detected so that it can then be confirmed what type of rhythm is present before committing the associated pulse generator to a response. Following the response, GPD will be reactivated to confirm persistent arrhythmia or sinus rhythm irrespective of heart rate. Should the initial rhythm be sinus tachycardia, then the program will remain active only while the trigger rate is exceeded, preventing an inappropriate paced response. In this way, diagnostic and monitoring functions of an implanted device would be significantly improved.

Satisfactory operation of apparatus embodying this invention is dependent on the stability of the sensing electrode, as even small movements of the electrode tip would be expected to produce differences in electrogram shape and therefore an apparently abnormal rhythm as assessed by electrogram GPD. In experiments, recordings obtained using temporary electrodes with conventional "passive" tips yielded stable electrogram morphology within each rhythm despite this and the postural and respiratory variations employed.

Insofar as tachycardia recognition is concerned, a feature of the apparatus of this invention is its ability to distinguish between different types of tachycardia so that pacing response may be varied, even if the heart rates are similar.

The principle behind apparatus embodying this invention will now be described in greater detail with reference to sinus rhythm. Thus, in a first step, electrograms are sensed in the usual manner, sensing generally only occurring at a signal frequency in the range of 0.016–1 kHz, with the preferred range being from 0.016 Hz –300 Hz, the electrograms being obtained during sinus rhythm and during abnormal rhythm(s) to be distinguished from sinus rhythm and from each other. The analog electrograms produced are then converted to digital form preferably using an analog to digital converter frequency of 1 kHz. The digital electrograms are then converted to a first differential form where the amplitudes of this processed signal are proportional to the gradients (slopes or slew-rates) of the original analog signal. The resultant sequence of amplitudes is then examined, examination taking place of both sinus beats and those abnormal beats which are to be distinguished therefrom and possibly from each other should more than one abnormal rhythm exist in the same patient. The recognition of one rhythm from another is allowed by the differences in the sequence of amplitudes of the processed signal which exist between signals obtained from different rhythms. Once recognition is achieved, then the response of the pulse generator can be dictated according to programming. This programming will provide or withhold stimuli in response to abnormal beats in order to restore beats matching normal sinus rhythm of the patient. The apparatus will be specific both to the patient and the location at which sensors are to be placed.

Put at its simplest, the concept of this invention involves comparison of the first differentials of the digital electrograms of each beat with what is established to be the first differential of the digitial electrograms for normal rhythm. As will be apparent from FIG. 2 of the accompanying drawings, each beat has gradients which will differ from each other in magnitude, polarity and interval. It may be sufficient for many purposes to rely merely on the magnitudes and polarity of the processed signals being compared. As already stated, it will generally be necessary to compare the sequence of the deflections within the processed signal. However, a particularly sophisticated form of control can be achieved if temporal scanning is additionally carried out with it being necessary for a particular sequence of deflections to be achieved within a particular time interval and in a particular order within that time interval to characterise an abnormal rhythm, i.e. a programmable window is utilised for comparison purposes, this being set to include whatever parts of the processed signal are desired.

BRIEF DESCRIPTION OF THE DRAWINGS

For a better understanding of the invention, and to show how the same can be carried into effect, reference will now be made, by way of example only, to the accompanying drawings wherein.

DESCRIPTION OF THE PREFERRED EMBODIMENTS

Figure 1:
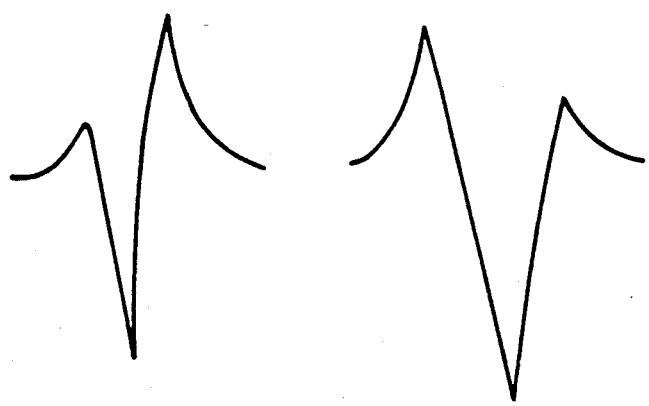
FIG. 1 is a schematic plot of amplitude against time for successive beats of a patient showing normal and abnormal beats.
Figure 2:
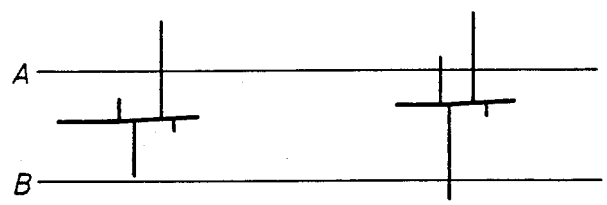
FIG. 2 shows an approximate first derivative of the signals of FIG. 1.

As can be seen from FIG. 1, in a typical case, each beat is shown to possess two peaks which differ in gradients and amplitudes between the respective beats. There are cases, however, when more than two peaks are likely to be encountered with each signal. Insofar as FIG. 1 is concerned, there are four slopes to each beat and thus referring to FIG. 2, the first differential of each slope will be correspondingly different as to magnitude, polarity and spacing from the other differentials associated with the beat. This derivative plot provides the means of distinguishing between sinus rhythm and an arrhythmia. An arrhythmia is identified by the different order of matching of threshold values, exemplified by lines A and B or failure to match such programmable threshold values within a programmable time interval.

Figure 3:
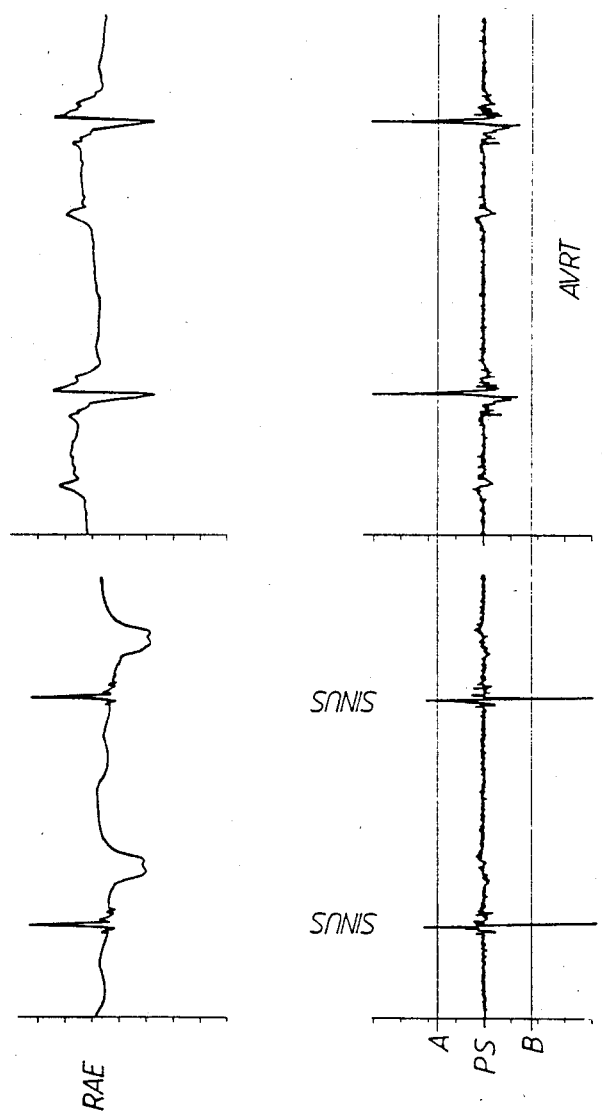
FIG. 3 shows in the upper panel a copy of experimentally obtained analog electrograms and in the lower panel a copy of the derivatives of the electrograms.

An analog electrogram obtained in practice is shown in the upper panel of FIG. 3 of the drawing, the lower panel showing processed signals. In FIG. 3, AVRT denotes atrio-ventricular re-entry tachycardia, PS denotes processed signals and RAE denotes atrial electrograms. The left panels denote sinus rhythm. Vertical labelling of "sinus" represents automatic detection of sinus rhythm, its absence confirming detection of altered rhythm. The threshold lines A and B illustrate the mechanism. For recognition of sinus rhythm, line A followed by line B both had to be crossed by the PS. Although the AVRT PS crossed line A, there was no subsequent deflection crossing line B within the programmed time interval so that cessation of sinus rhythm was detected.

In practical determinations to obtain results of the type shown in FIG. 3, electrograms have been recorded from 1 cm bipoles in the atrium and either 1 cm bipoles or 0.5 cm bipoles at the right ventricular apex (RVA), a single surface ECG channel being recorded simultaneously. The intracardiac recordings were made between either DC to 300 Hz or 0.016 Hz to 300 Hz using a Biodata P400 amplifier onto a Racal store 7 tape recorder. The analog electrograms recorded were then digitised at a sampling frequency of 1 kHz. This relatively low sampling frequency was chosen firstly because the electrogram frequency spectrum contains little useful information amongst high frequencies and secondly with a view to implantability of a pacemaker embodying the invention and the need to consider battery conservation. The digital electrogram was then converted into a form closely resembling its first time derivative where the amplitudes of the derived signal were proportional to the rates of change of the original electrogram. The derived signal was then analysed by a gradient pattern detection program of the invention which examined for the sequential changes of gradients contained within it. This sequence was then compared with a reference sequence obtained during sinus rhythm and/or other abnormal rhythms, recognition being based on the difference between the sequences. GPD was triggered when certain individually adjustable criteria were met by the derived signal and switched off after a programmable time interval. The triggering criteria consisted of the initial deflection of the processed signal (of either polarity) being greater than a threshold for amplitude and this being sustained for a preset minimum number of sampling points. Satisfaction of these requirements ensured that extraneous "noise" was not misinterpreted. The sequence of gradients within the original electrogram was detected by analysis of the amplitudes of the subsequent deflections of the processed signal. Pathological tachycardia was detected when either the polarity and/or the amplitudes of the deflections and/or their duration and/or the intervals between them differed from those seen with sinus electrograms which can be seen to be clearly the case when reference is made to the lower panels of FIG. 3 of the drawings. Variations of respiration, posture and sinus rate have been found not to alter atrial electrogram morphology in patients in such a way as to affect recognition by GPD despite the fact that there may have been noticeable changes in analog electrogam amplitudes in patients. Moreover, similar types of results have been obtained when producing ventricular electrograms.

Figure 4:
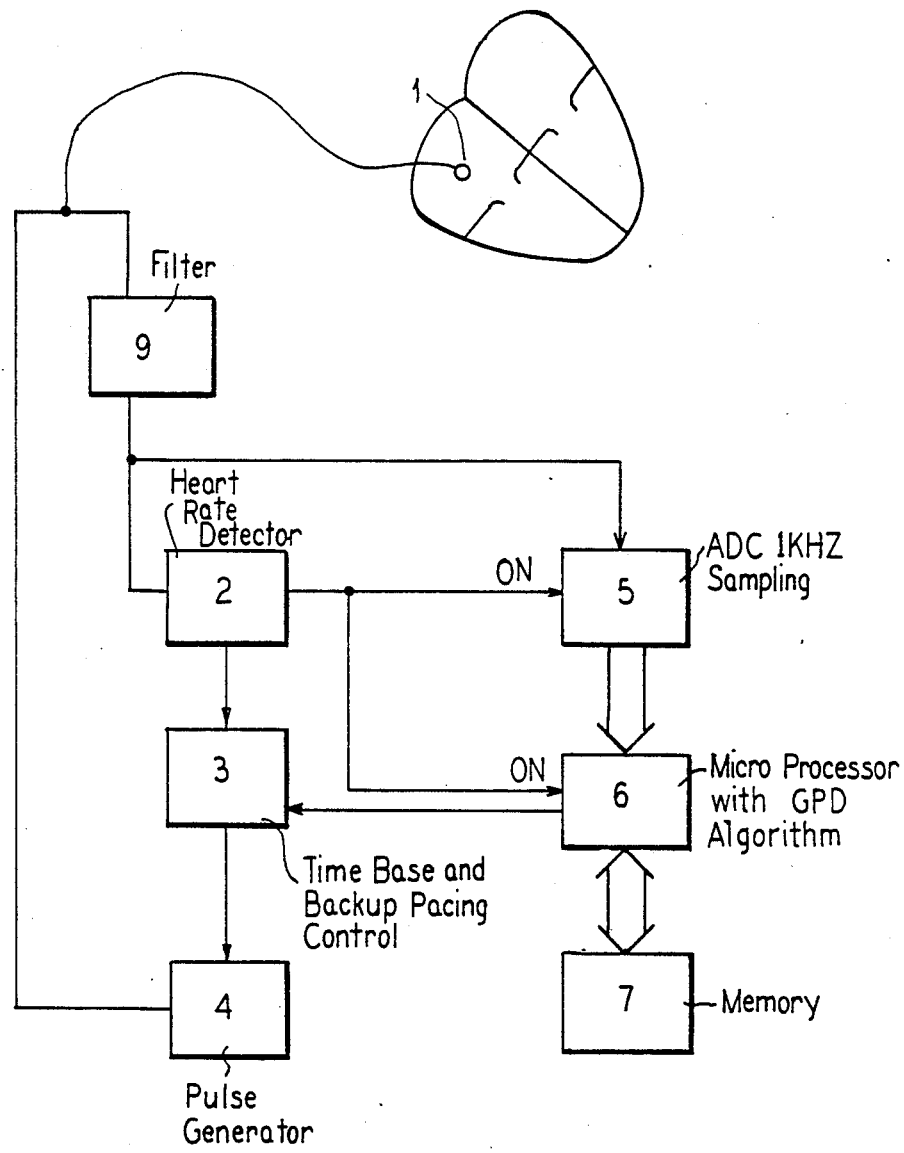
FIG. 4 is a block diagram of a cardiac implant embodying this invention.
Figure 5:
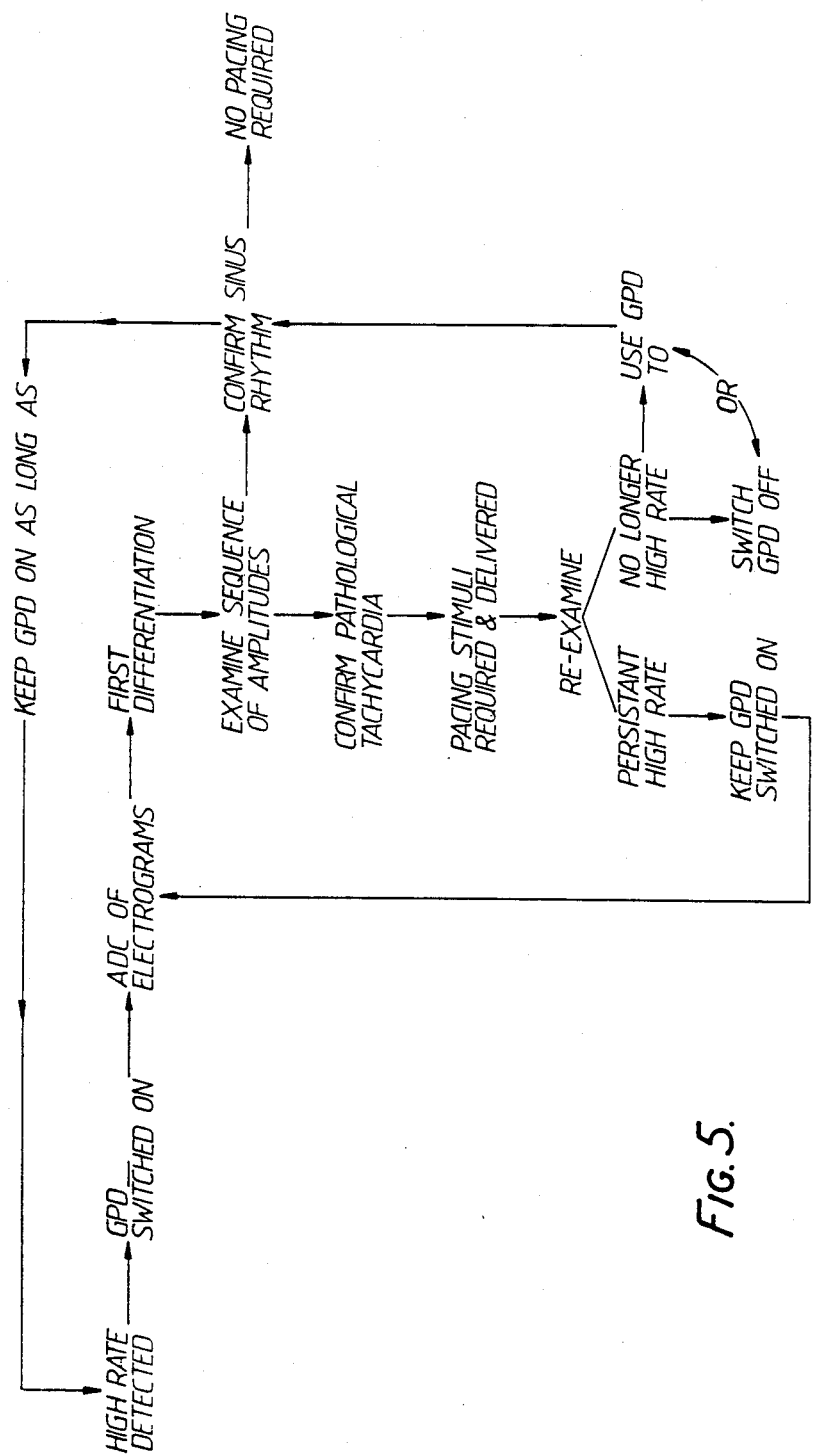
FIG. 5 is a flow diagram of the steps involved in recognising pathological tachycardia in a cardiac implant embodying this invention.

Finally, FIGS. 4 and 5 show practical embodiments of the invention and should be viewed in conjunction with each other.

As shown in FIG. 4, an implant located at for example an atrial location 1 will monitor atrial rate by means of a bipolar electrocardiographic electrode lead at all times using a conventional heart beat detector 2 having time-base and back up pacing control 3 whose operation is directed by a microprocessor 6 having a memory 7. pass filter 9 connected between location 1 and heart rate detector 2 operates to attenuate all signals outside the range 0.016 to 300 Hz. Should a high atrial rate be detected, then the A.D.C. 5 and the gradient pattern detection algorithm within microprocessor 6 is switched on so that electrograms entering microprocessor 6 are digitised and the digitised signals are subjected to a first differentiation by the microprocessor 6. The sequence, amplitude, polarity and duration (width) of the deflections and the intervals between deflections of the processed signals obtained are examined. With the assistance of memory 7, these values are compared with equivalent values characteristic of sinus rhythm and/or other abnormal rhythms obtained by similar procedure. According to the diagnosis by the microprocessor 6, pacing stimuli will be delivered to or withheld from the patient. If the values indicate pathological tachycardia, then pacing stimuli will be required and will be delivered from pulse generator 4 except when retrograde atrial depolarisation should be ignored by a dual chamber pacemaker for which purpose, the memory is programmed. The pacing stimuli will be specific for the type or types of pathological tachycardia indicated by the identification of the arrhythmia(s) with the derivative signals known to be characteristic of such arrhythmias and pre-programmed in the device. The purpose of the delivered stimuli is to attempt to terminate the arrhythmia(s) and after the stimulus(i) has been delivered, GPD will be switched on again and the process will be repeated to confirm whether pacing has been successful. If there is a persistent high heart rate, then the GPD will be kept switched on and further stimuli will be delivered if appropriate until continuing re-examination shows that there is no longer a high pulse rate or that the high rate is caused by sinus tachycardia. Whenever re-examination shows that there is no longer a high heart rate, either the GPD will be switched off or the GPD may be kept operating in case there should be a resurgence of arrhythmia, although such operation will be wasteful of the battery supplying power to the system.

When a high cardiac rhythm rate is detected, the gradient pattern detector is switched on (analog-to-digital converter 5 and microprocessor 6 shown in FIG. 4). Signals from the filter 9 are then converted to digital signals and a first differentiation is performed by the microprocessor 6. The microprocessor 6 examines the sequence of the signal patterns subjected to the differentiation in comparison with normal signal patterns stored in memory 7. If sinus rhythm is confirmed, no pacing is required. On the other hand, if pathological tachycardis is confirmed by the comparison, pacing stimuli is required and is delivered via the time base and back-up pacer control 3 and pulse generator 4. As long as the high rate persists, the gradient pattern detector is switched on. If the high rate no longer exists, the gradient pattern detector is switched off.

The procedure shown in FIG. 5 may be modified for use in dual chamber pacemakers where a positive identification of an abnormal rhythm might lead to withholding pacing. If the possibility of non-sinus atrial rhythm is suspected, for example with retrograde atrial depolarisation after a premature ventricular beat, then ventricular pacing would be withheld, whereas if the next atrial depolarisation after such a ventricular beat was confirmed to be of sinus origin, then a ventricular pacing stimulus would be delivered after the programmed AV delay.

Although various minor changes and modifications might be proposed by those skilled in the art, it will be understood that we wish to include within the scope of the claims of the patent warranted hereon, all such changes and modifications as reasonably come within my contribution to the art.

I claim as my invention:

1. An apparatus for recognizing cardiac arrythmias, comprising:
   sensing electrode means for attachment to at least one cardiac sensing location and for producing cardiac signals;
   filter means connected to the sensing electrode means for filtering the cardiac signals such that undesired signals lying outside a given frequency range are attenuated;
   a heart rate detector means connected to receive the cardiac signals from the filter means for detecting a high cardiac signal rate above a predetermined level and providing an output in response thereto;
   an analog-to-digital converter means and a gradient pattern detection and comparison means connected to said output of the heart rate detector means to be activated when the high cardiac rate is detected, the analog-to-digital converter means also being connected to receive the cardiac signals from the filter means, and and the gradient pattern detection and comparison means being connected to receive digital signals from the analog-to-digital converter means;

said gradient pattern detection and comparison means having a memory means for storing differentiated normal signals of a as normal cardiac rhythm; and said gradient pattern detection and comparison means performing a first differentiation of the digital signals from the analog-to-digital converter means, and comparing these differentiated signals as to amplitude, polarity, duration, separation, and sequence to the differential normal signals stored in the memory means, and providing an output based on the comparison which is determinative of whether or not pacing should be initiated.

2. An apparatus according to claim 1 wherein a time base and back up pacing control means with a connected pulse generator means is connected to an output of the heart rate detector means and to said output of the gradient pattern detection and comparison means for initiating said pacing depending upon the output of the detection and comparison means, said pulse generator means having an output at which a pacing signal is provided.

3. An apparatus according to claim 1 wherein the filter means attenuates signals outside a range of 0.016 Hz to 1 KHz.

4. An apparatus according to claim 3 wherein the filter means attenuates signals outside a range of 0.016 Hz to 300 Hz.

5. An apparatus according to claim 4 wherein the analog-to-digital converter means digitizes at a sampling frequency of 1 KHz.

6. An apparatus according to claim 1 wherein said gradient pattern detection and comparison means comprises means for generating a temporal window and for comparing in said temporal window a pre-established sequence of differential signal deflections stored in said memory means according to their amplitudes, duration, separation and polarities.

7. An apparatus for recognizing cardiac arrythmias, comprising:

sensing electrode means for attachment to at least one cardiac sensing location and for producing cardiac signals;

filter means connected to the sensing electrode means for filtering the cardiac signals such that undesired signals lying outside a given frequency range are attenuated;

a heart rate detector means connected to receive the cardiac signals from the filter means for detecting a high cardiac signal rate above a predetermined level and providing an output in response thereto;

an analog-to-digital converter means and a gradient pattern detection and comparison means connected to said output of the heart rate detector means to be activated when the high cardiac rate is detected, the analog-to-digital converter means also being connected to receive the cardiac signals from the filter means and the gradient pattern detection and comparison means being connected to receive digital signals from the analog-to-digital converter means;

said gradient pattern detection and comparison means having a memory means for storing differentiated normal signals of a normal cardiac rhythm; and said gradient pattern detection and comparison means performing a first differentiation of the digital signals from the analog-to-digital converter means, and comparing these differentiated signals as to amplitude, polarity, and sequence to the differentiated normal signals stored in the memory means, and providing an output based on the comparison which is determinative of whether or not pacing should be initiated.

* * * * *